United States Patent [19]
Dubief et al.

[11] Patent Number: 6,011,126
[45] Date of Patent: Jan. 4, 2000

[54] TOPICAL COMPOSITION COMPRISING THE COMBINATION OF A POLYMER WITH A NON-SILICONE SKELETON WITH SILICONE GRAFTS AND OF A POLYMER WITH A POLYSILOXANE SKELETON WITH NON-SILICONE GRAFTS

[75] Inventors: Claude Dubief, Le Chesnay; Christine Dupuis, Paris, both of France

[73] Assignee: L'Oreal, Paris, France

[21] Appl. No.: 09/089,446

[22] Filed: Jun. 3, 1998

Related U.S. Application Data

[63] Continuation of application No. 08/720,530, Sep. 30, 1996, abandoned.

[30] Foreign Application Priority Data

Sep. 29, 1995 [FR] France .................................. 95-11487

[51] Int. Cl.[7] .................................................. C08F 283/12
[52] U.S. Cl. ...................... 525/477; 424/70.12; 526/279
[58] Field of Search ........................... 525/477; 526/279; 424/70.12

[56] References Cited

U.S. PATENT DOCUMENTS

| 4,693,935 | 9/1987 | Mazurek ................................ 428/352 |
| 4,728,571 | 3/1988 | Clems et al. ............................ 428/352 |
| 4,972,037 | 11/1990 | Garbe et al. ............................ 526/245 |
| 5,106,609 | 4/1992 | Bolich, Jr. et al. ....................... 424/70 |
| 5,362,485 | 11/1994 | Hayama et al. ........................... 424/70 |
| 5,565,193 | 10/1996 | Midha et al. ......................... 424/70.12 |

FOREIGN PATENT DOCUMENTS

| 0 388 582 | 9/1990 | European Pat. Off. . |
| 0 412 704 | 2/1991 | European Pat. Off. . |
| 0 412 707 | 2/1991 | European Pat. Off. . |
| 0 412 710 | 2/1991 | European Pat. Off. . |
| 0 582 152 | 2/1994 | European Pat. Off. . |
| WO 93/23009 | 11/1993 | WIPO . |
| WO 93/23446 | 11/1993 | WIPO . |
| WO 95/00108 | 1/1995 | WIPO . |
| WO 95/00578 | 1/1995 | WIPO . |
| WO 95/03776 | 2/1995 | WIPO . |
| WO 95/05880 | 3/1995 | WIPO . |

*Primary Examiner*—Margaret G. Moore
*Attorney, Agent, or Firm*—Finnegan, Henderson, Farabow, Garrett & Dunner, L.L.P.

[57] ABSTRACT

The present invention relates to a cosmetic or dermatological composition for the treatment of keratinous substances, in particular human hair, comprising, in a cosmetically or dermatologically acceptable medium, at least one polymer with a non-silicone organic skeleton grafted by monomers containing a polysiloxane and at least one polymer with a polysiloxane skeleton grafted by non-silicone organic monomers and to its uses. The compositions according to the invention are used in particular as product which are to be rinsed or as products which are not to be rinsed, in particular for washing, caring for or conditioning the hair, form retention of the hairstyle or shaping of the hairstyle.

54 Claims, No Drawings that were better than those obtained by
TOPICAL COMPOSITION COMPRISING THE COMBINATION OF A POLYMER WITH A NON-SILICONE SKELETON WITH SILICONE GRAFTS AND OF A POLYMER WITH A POLYSILOXANE SKELETON WITH NON-SILICONE GRAFTS This is a continuation of application Ser. No. 08/720,530 filed Sep. 30, 1996, now abandoned.

The present invention relates to a cosmetic or dermatological composition for the treatment of keratinous substances, in particular human hair, comprising at least one polymer with a non-silicone organic skeleton grafted by monomers containing a polysiloxane and at least one polymer with a polysiloxane skeleton grafted by non-silicone organic monomers and to its uses.

Polymers with a non-silicone organic skeleton grafted by monomers containing a polysiloxane are known in the state of the art, such as those described in U.S. Pat. Nos. 4,693,935 and 4,728,571 and Patent Applications EP-A-0,412,704, EP-A-0,412,707, EP-A-0,640,105 and WO 95/00578, which are incorporated herein by reference. These polymers are used in hair care for their styling properties.

Polymers with a polysiloxane skeleton grafted by non-silicone organic monomers are also known in the state of the art, which are preferentially chosen from those described in Applications EP-A-0,582,152 and WO 93/23009, which are incorporated herein by reference. They are also used in hair care for their styling properties.

The inventors have surprisingly discovered that, by combining at least one polymer with a non-silicone organic skeleton grafted by monomers containing a polysiloxane with at least one polymer containing a polysiloxane skeleton grafted by non-silicone organic monomers, styling properties were obtained that were better than those obtained by each polymer used alone; this is reflected by a better interfibre adhesion. The inventors have also discovered that the combination of grafted silicone polymers of the invention improved the smoothness to the touch after application with respect to each polymer of the combination used alone.

The composition according to the invention is therefore essentially characterized in that it contains, in a cosmetically or dermatologically acceptable medium, at least one polymer with a non-silicone organic skeleton grafted by monomers containing a polysiloxane and at least one polymer with a polysiloxane skeleton grafted by non-silicone organic monomers.

As used herein, silicone or polysiloxane is understood to denote, in conformity with what is generally accepted, any organosilicon polymer or oligomer with a branched or crosslinked, linear or cyclic structure of variable molecular weight obtained by polymerization and/or polycondensation of suitably functionalized silanes and essentially composed of a repetition of main units in which the silicon atoms are connected to one another via oxygen atoms (siloxane bond $\equiv$Si—O—Si$\equiv$), optionally substituted hydrocarbon radicals being directly bonded via a carbon atom to the said silicon atoms. The most common hydrocarbon radicals include, for example, alkyl radicals, especially $C_1$–$C_{10}$ alkyl radicals and in particular methyl radicals, fluoroalkyl radicals, aryl radicals, and in particular phenyl radicals, and alkenyl radicals, and in particular vinyl radicals; other types of radicals capable of being bonded either directly or via a hydrocarbon radical to the siloxane chain are in particular hydrogen, halogens, and in particular chlorine, bromine or fluorine, thiols, alkoxy radicals, polyoxyalkylene (or polyether) radicals and in particular polyoxyethylene and/or polyoxypropylene radicals, hydroxyl or hydroxyalkyl radicals, amino groups, which may or may not be substituted, amide groups, acyloxy or acyloxyalkyl radicals, hydroxyalkylamino or aminoalkyl radicals, quaternary ammonium groups, amphoteric or betaine groups or anionic groups, such as carboxylate, thioglycolate, sulphosuccinate, thiosulphate, phosphate and sulphate groups, this list, of course, being in no way limiting (so-called "organomodified" silicones).

As used herein, "polysiloxane macromer" is understood to denote, in conformity with what is generally accepted, any monomer containing, in its structure, a polymer chain of the polysiloxane type.

The polymers with a non-silicone organic skeleton grafted by monomers containing a polysiloxane in accordance with the present invention are composed of an organic main chain formed from organic monomers not containing silicone, on which is grafted, within the said chain and optionally at least one of its ends, at least one polysiloxane macromer.

The non-silicone organic monomers constituting the main chain of the grafted silicone polymer can be chosen from monomers with ethylenic unsaturation polymerizable by the radical route, monomers polymerizable by polycondensation, such as those forming polyamides, polyesters or polyurethanes, or monomers with ring opening, such as those of the oxazoline or caprolactone type.

The polymers with a non-silicone organic skeleton grafted by monomers containing a polysiloxane in accordance with the present invention can be obtained by any means known to a person skilled in the art, in particular by reaction between (i) a starting polysiloxane macromer correctly functionalized on the polysiloxane chain and (ii) one or a number of non-silicone organic compounds, themselves correctly functionalized by a functional group which is capable of reacting with the functional group or groups carried by the said silicone with the formation of a covalent bond; a classic example of such a reaction is the radical reaction between a vinyl group carried on one of the ends of the silicone and a double bond of a monomer with ethylenic unsaturation of the main chain.

The polymers with a non-silicone organic skeleton grafted by monomers containing a polysiloxane in accordance with the invention are more preferably chosen from those described in U.S. Pat. Nos. 4,693,935, 4,728,571 and 4,972,037 and Patent Applications EP-A-0,412,704, EP-A-0,412,707, EP-A-0,640,105 and WO 95/00578, all of which are incorporated herein by reference. They concern copolymers obtained by radical polymerization from monomers with ethylenic unsaturation and from silicone macromers having an end vinyl group or alternatively the copolymers obtained by reaction of a polyolefin comprising functionalized groups and of a polysiloxane macromer having an end functional group which is reactive with the said functionalized groups.

A specific family of grafted silicone polymers that is suitable for the implementation of the present invention is composed of the grafted silicone copolymers comprising:

a) from 0 to 98 weight % of at least one lipophilic monomer (A) of low lipophilic polarity with ethylenic unsaturation which is polymerizable by the radical route;

b) from 0 to 98 weight % of at least one polar hydrophilic monomer (B) with ethylenic unsaturation which is copolymerizable with the monomer or monomers of the type (A);

c) from 0.01 to 50 weight % of at least one polysiloxane macromer (C) of general formula:

$$X(Y)_n Si(R)_{3-m} Z_m \quad (I)$$

where:
X denotes a vinyl group which is copolymerizable with the monomers (A) and (B);
Y denotes a group with divalent bonding;
R denotes a hydrogen, a $C_1$–$C_6$ alkyl or alkoxy or a $C_6$–$C_{12}$ aryl;
Z denotes a monovalent polysiloxane unit having a number-average molecular weight of at least 500;
n is 0 or 1; and
m is an integer ranging from 1 to 3,
the percentages being calculated with respect to the total weight of the monomers (A), (B) and (C).

These polymers, and processes for the preparation thereof, are described in U.S. Pat. Nos. 4,693,935, 4,728,571 and 4,972,037 and Patent Applications EP-A-0,412,704, EP-A-0,412,707 and EP-A-0,640,105. They have a number-average molecular weight preferably ranging from 10,000 to 2,000,000 and preferably a glass transition temperature Tg or a crystalline melting temperature Tm of at least −20° C.

Mention may be made, as examples of lipophilic monomers (A), of esters of acrylic or methacrylic acid with $C_1$–$C_{18}$ alcohols; styrene; polystyrene macromers; vinyl acetate; vinyl propionate; α-methylstyrene; tert-butylstyrene; butadiene; cyclohexadiene; ethylene; propylene; vinyltoluene; esters of acrylic or methacrylic acid with 1,1-dihydroperfluoroalkanol or with its homologues; esters of acrylic or methacrylic acid with ω-hydrofluoroalkanol; esters of acrylic or methacrylic acid with fluoroalkylsulphoamidoalcohol; esters of acrylic or methacrylic acid with fluoroalkyl alcohol; esters of acrylic or methacrylic acid with alcohol fluoroether; or their mixtures.

The preferred monomers (A) are chosen from the group composed of n-butyl methacrylate, isobutyl methacrylate, tert-butyl acrylate, tert-butyl methacrylate, 2-ethylhexyl methacrylate, methyl methacrylate, 2-(N-methylperfluorooctanesulphonamido)ethyl acrylate, 2-(N-butylperfluorooctanesulphonamido)ethyl acrylate and their mixtures.

Mention may be made, as examples of polar monomers (B), of acrylic acid, methacrylic acid, N,N-dimethylacrylamide, dimethylaminoethyl methacrylate, quaternized dimethylaminoethyl methacrylate, (meth)acrylamide, N-t-butylacrylamide, maleic acid, maleic anhydride and its half-esters, hydroxyalkyl (meth)acrylates, diallyldimethylammonium chloride, vinylpyrrolidone, vinyl ethers, maleimides, vinylpyridine, vinylimidazole, polar heterocyclic vinyl compounds, styrenesulphonate, allyl alcohol, vinyl alcohol, vinylcaprolactam or their mixtures. The preferred monomers (B) are chosen from the group composed of acrylic acid, N,N-dimethylacrylamide, dimethylaminoethyl methacrylate, quaternized dimethylaminoethyl methacrylate, vinylpyrrolidone and their mixtures.

The preferred polysiloxane macromers (C) of formula (I) are chosen from those corresponding to the following general formula (II):

$$CHR^1=CR^2-\overset{O}{\underset{\|}{C}}-O-(CH_2)_q-(O)_p-Si(R^3)_{3-m}(O-\underset{CH_3}{\overset{CH_3}{\underset{|}{\overset{|}{Si}}}})_r-R^4$$

$R^1$ is hydrogen or —COOH (preferably hydrogen);
$R^2$ is hydrogen, methyl or —$CH_2$COOH (preferably methyl);
$R^3$ is $C_1$–$C_6$ alkyl, alkoxy or alkylamino, $C_6$–$C_{12}$ aryl or hydroxyl (preferably methyl);
$R^4$ is $C_1$–$C_6$ alkyl, alkoxy or alkylamino, $C_6$–$C_{12}$ aryl or hydroxyl (preferably methyl);
q is an integer from 2 to 6 (preferably 3);
p is 0 or 1;
r is an integer from 5 to 700;
m is an integer ranging from 1 to 3 (preferably 1).

Use is more particularly made of the polysiloxane macromers of formula:

$$CH_2=\underset{CH_3}{\overset{}{\underset{|}{C}}}-\overset{O}{\underset{\|}{C}}-O-(CH_2)_3-\underset{CH_3}{\overset{CH_3}{\underset{|}{\overset{|}{Si}}}}-O\left[\underset{CH_3}{\overset{CH_3}{\underset{|}{\overset{|}{Si}}}}-O\right]_n\underset{CH_3}{\overset{CH_3}{\underset{|}{\overset{|}{Si}}}}-(CH_2)_3-CH_3$$

a number ranging from 5 to 700.

A specific embodiment of the invention comprises the use of a copolymer capable of being obtained by radical polymerization from the mixture of monomers comprising:

a) 60 weight % of tert-butyl acrylate;
b) 20 weight % of acrylic acid;
c) 20 weight % of silicone macromer of formula:

$$CH_2=\underset{CH_3}{\overset{}{\underset{|}{C}}}-\overset{O}{\underset{\|}{C}}-O-(CH_2)_3-\underset{CH_3}{\overset{CH_3}{\underset{|}{\overset{|}{Si}}}}-O\left[\underset{CH_3}{\overset{CH_3}{\underset{|}{\overset{|}{Si}}}}-O\right]_n\underset{CH_3}{\overset{CH_3}{\underset{|}{\overset{|}{Si}}}}-(CH_2)_3-CH_3$$

g a number ranging from 5 to 700, the percentages by weight being calculated with respect to the total weight of the monomers.

Another specific embodiment of the invention comprises the use of a copolymer capable of being obtained by radical polymerization from the mixture of monomers comprising:

a) 80 weight % of tert-butyl acrylate;
b) 20 weight % of silicone macromer of formula:

$$CH_2=\underset{CH_3}{\overset{}{\underset{|}{C}}}-\overset{O}{\underset{\|}{C}}-O-(CH_2)_3-\underset{CH_3}{\overset{CH_3}{\underset{|}{\overset{|}{Si}}}}-O\left[\underset{CH_3}{\overset{CH_3}{\underset{|}{\overset{|}{Si}}}}-O\right]_n\underset{CH_3}{\overset{CH_3}{\underset{|}{\overset{|}{Si}}}}-(CH_2)_3-CH_3$$

a number ranging from 5 to 700, the percentages by weight being calculated with respect to the total weight of the monomers.

Another specific family of silicone polymers suitable for the implementation of the present invention is composed of the grafted silicone copolymers capable of being obtained by reactive extrusion of a polysiloxane macromer having an end reactive functional group with a polymer of the polyolefin type containing reactive groups capable of reacting with the end reactive functional group of the polysiloxane macromer in order to form a covalent bond which enables the silicone to be grafted to the main chain of the polyolefin. These polymers, and the process for the preparation thereof, are described in Patent Application WO 95/00578, incorporated by reference herein.

The reactive polyolefins are preferably chosen from polyethylenes or polymers of monomers derived from ethylene, such as propylene, styrene, alkylstyrene, butylene, butadiene, (meth)acrylates, vinyl esters or equivalents, containing reactive functional groups capable of reacting with the end functional group of the polysiloxane macromer. They are more preferably chosen from copolymers of ethylene or of ethylene derivatives and of monomers chosen from those containing a carboxyl functional group, such as (meth)acrylic acid; those containing an acid anhydride functional group, such as the anhydride of maleic acid; those containing an acid chloride functional group, such as the chloride of (meth)acrylic acid; those containing an ester functional group, such as the esters of (meth)acrylic acid; or those containing an isocyanate functional group.

The silicone macromers are preferably chosen from polysiloxanes containing a functionalized group, at the end of the polysiloxane chain or close to the end of the said chain, chosen from the group composed of alcohols, thiols, epoxy groups or primary and secondary amines and more preferably from those corresponding to the general formula (III):

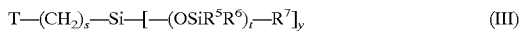

T—(CH$_2$)$_s$—Si—[—(OSiR$^5$R$^6$)$_t$—R$^7$]$_y$ (III)

in which T is chosen from the group composed of NH$_2$, NHR', an epoxy functional group, OH or SH; R$^5$, R$^6$, R$^7$ and R' independently denote a C$_1$–C$_6$ alkyl, phenyl, benzyl or C$_6$–C$_{12}$ alkylphenyl or hydrogen; s is a number from 2 to 100; t is a number from 0 to 1000 and y is a number from 1 to 3. They have a number-average molecular weight preferably ranging from 5000 to 300,000, more preferably from 8000 to 200,000 and still more preferably from 9000 to 40,000.

According to the present invention, the polymer or polymers with a polysiloxane skeleton grafted by non-silicone organic monomers comprise a main silicone (or polysiloxane ($\equiv$Si—O—)$_n$) chain on which is grafted, within the chain and optionally at at least one of its ends, at least one organic group not containing silicone.

The polymers with a polysiloxane skeleton grafted by non-silicone organic monomers according to the invention can be existing commercial products or alternatively be obtained according to any means known to the person skilled in the art, in particular by reaction between (i) a starting silicone correctly functionalized on one or a number of these silicon atoms and (ii) a non-silicone organic compound itself correctly functionalized by a functional group which is capable of reacting with the functional group or groups carried by the said silicone with the formation of a covalent bond; a classic example of such a reaction is the hydrosilylation reaction between $\equiv$Si—H groups and CH$_2$=CH— vinyl groups or alternatively the reaction between —SH thiol functional groups and these same vinyl groups.

Examples of polymers with a polysiloxane skeleton grafted by non-silicone organic monomers suitable for the implementation of the present invention, as well as their specific method of preparation, are in particular described in Patent Applications EP-A-0,582,152, WO 93/23009 and WO 95/03776, the teachings of which are incorporated herein by reference.

According to a particularly preferred embodiment of the present invention, the polymer with a polysiloxane skeleton grafted by non-silicone organic monomers used comprises the result of the radical copolymerization between, on the one hand, at least one anionic non-silicone organic monomer exhibiting an ethylenic unsaturation and/or one hydrophobic non-silicone organic monomer exhibiting an ethylenic unsaturation and, on the other hand, a silicone exhibiting, in its chain, at least one functional group capable of reacting with the said ethylenic unsaturations of the said non-silicone monomers with the formation of a covalent bond, in particular thiol functional groups.

According to the present invention, the anionic monomers with ethylenic unsaturation are preferably chosen, alone or as mixtures, from linear or branched unsaturated carboxylic acids, optionally partially or completely neutralized in the form of a salt, it being possible for this or these unsaturated carboxylic acids to be more particularly acrylic acid, methacrylic acid, maleic acid, maleic anhydride, itaconic acid, fumaric acid and crotonic acid. Suitable salts are in particular the alkali metal, alkaline-earth metal and ammonium salts. It should be noted that, likewise, in the final grafted silicone polymer, the organic group of anionic nature which comprises the result of the radical (homo)polymerization of at least one anionic monomer of unsaturated carboxylic acid type can, after reaction, be post-neutralized with a base (sodium hydroxide, ammonia, and the like) in order to convert it to the form of a salt.

According to the present invention, the hydrophobic monomers with ethylenic unsaturation are preferably chosen, alone or as mixtures, from alkanol acrylic acid esters and/or alkanol methacrylic acid esters. The alkanols are preferably C$_1$–C$_{18}$ alkanols and more particularly C$_1$–C$_{12}$ alkanols. The preferred monomers are chosen from the group composed of isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth)acrylate, tridecyl (meth)acrylate, stearyl (meth)acrylate or their mixtures.

A family of polymers with a polysiloxane skeleton grafted by non-silicone organic monomers that is particularly well suited to the implementation of the present invention is composed of silicone polymers containing, in their structure, the following unit of formula (IV):

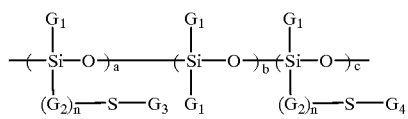

wherein the G$_1$ radicals, which are identical or different, represent hydrogen or a C$_1$–C$_{10}$ alkyl radical or alternatively a phenyl radical; the G$_2$ radicals, which are identical or different, represent a C$_1$–C$_{10}$ alkylene group; G$_3$ represents a polymer residue resulting from the (homo)polymerization of at least one anionic monomer with ethylenic unsaturation; G$_4$ represents a polymer residue resulting from the (homo) polymerization of at least one hydrophobic monomer with ethylenic unsaturation; m and n are equal to 0 or 1; a is an integer ranging from 0 to 50; b is an integer ranging from 10 to 350 and c is an integer ranging from 0 to 50, with the proviso that one of the parameters a and c is other than 0.

The above unit of formula (IV) preferably exhibits at least one, and still more preferably all, of the following characteristics:

the G$_1$ radicals denote an alkyl radical, preferably the methyl radical;

n is not zero and the G$_2$ radicals represent a divalent C$_1$–C$_3$ radical, preferably a propylene radical;

G$_3$ represents a polymer radical resulting from the (homo) polymerization of at least one monomer of the carboxylic acid with ethylenic unsaturation type, preferably acrylic acid and/or methacrylic acid;

G$_4$ represents a polymer radical resulting from the (homo) polymerization of at least one monomer of the (C$_1$–C$_{10}$)alkyl (meth)acrylate type, preferably isobutyl or methyl (meth)acrylate.

Examples of silicone polymers corresponding to the formula (IV) are in particular polydimethylsiloxanes (PDMS)

on which are grafted, via a connecting link of thiopropylene type, mixed polymer units of the poly((meth)acrylic acid) type and of the poly(methyl (meth)acrylate) type.

Other examples of silicone polymers corresponding to the formula (IV) are in particular polydimethylsiloxanes (PDMS) on which are grafted, via a connecting link of thiopropylene type, polymer units of the poly(isobutyl (meth)acrylate) type.

The number-average molecular mass of the polymers with a polysiloxane skeleton grafted by non-silicone organic monomers of the invention preferably varies from approximately 10,000 to 1,000,000 and still more preferably from approximately 10,000 to 100,000.

The polymers with a non-silicone organic skeleton grafted by monomers containing a polysiloxane are preferably used in an amount ranging from 0.01 to 15 weight % of the total weight of the composition. More preferentially still, this amount varies from 0.5 to 10 weight %.

The polymers with a polysiloxane skeleton grafted by non-silicone organic monomers are preferably used in an amount ranging from 0.01 to 20 weight % of the total weight of the composition. More preferably, this amount varies from 0.1 to 15 weight % and still more preferably from 0.5 to 10 weight %.

The cosmetically or dermatologically acceptable medium is preferably composed of water or a mixture of water and of cosmetically acceptable solvents, such as monoalcohols, polyalcohols, glycol ethers or fatty acid esters, which can be used alone or as a mixture.

Mention may more particularly be made of lower alcohols, such as ethanol or isopropanol, polyalcohols, such as diethylene glycol, or glycol ethers, such as the alkyl ethers of glycol or of diethylene glycol.

The grafted silicone polymers according to the invention can be dissolved in the cosmetically acceptable medium or used in the form of an aqueous dispersion of particles.

The composition of the invention can also contain at least one additive chosen from thickeners, fatty acid esters, esters of fatty acids and of glycerol, silicones, surfactants, fragrances, preservatives, sunscreening agents, proteins, vitamins, polymers, vegetable, animal, mineral or synthetic oils and any other additive conventionally used in the cosmetics field.

These additives are present in the composition according to the invention in proportions which preferably range from 0 to 20 weight % with respect to the total weight of the composition. The exact amount of each additive depends on its nature and is easily determined by the person skilled in the art.

Of course, the person skilled in the art will take care to choose the optional compound or compounds to be added to the composition according to the invention so that the advantageous properties intrinsically attached to the composition in accordance with the invention are not, or not substantially, detrimentally affected by the envisaged addition.

The compositions according to the invention can be provided in the gel, milk, cream, more or less thickened lotion or foam form.

They are more particularly hair setting lotions, blow drying lotions, fixing compositions (lacquers) and styling lotions. The lotions can be packaged in various forms, in particular in vaporizers or pump-action sprays or in aerosol containers, in order to provide for application of the composition in the vaporized form or in the foam form. Such packaging forms are indicated, for example, when it is desired to obtain a spray, a lacquer or a foam for fixing or treating the hair.

The compositions can also be shampoos or compositions which are or are not to be rinsed, to be applied before or after shampooing, dyeing, bleaching, permanent waving or hair straightening.

When the composition according to the invention is packaged in the form of an aerosol for the purpose of obtaining a lacquer or an aerosol foam, it comprises at least one propellent agent which can be chosen from volatile hydrocarbons, such as n-butane, propane, isobutane or pentane, or a chlorinated and/or fluorinated hydrocarbon and their mixtures. It is also possible to use, as a propellent agent, carbon dioxide gas, nitrous oxide, dimethyl ether, nitrogen, compressed air and their mixtures.

A further subject of the invention is a non-therapeutic process for the treatment of keratinous substances, such as hair, which comprises the application to the latter of a composition as defined above and then optionally rinsing with water.

The invention will now be more completely illustrated using the following examples which should not be regarded as limiting it to the embodiments described.

EXAMPLES

Example 1
Pump-Action Styling Spray

| | |
|---|---|
| - Grafted silicone polymer of formula (IV) of polymethyl/methyl-siloxane structure with poly(meth-acrylic acid)-3-thiopropyl groups and poly(methyl methacrylate)-3-thiopropyl groups | 3 g of AM |
| - Grafted silicone polymer of structure (1) as defined below | 3 g of AM |
| - Aminomethylpropanol, 100% neutralization of the two grafted silicone polymers | q.s. for pH 7.5 |
| - Ethanol | q.s. for 100 g |

Structure (1)

Copolymer obtained by radical polymerization from the mixture of monomers consisting of:

a) 60 weight % of tert-butyl acrylate;

b) 20 weight % of acrylic acid;

c) 20 weight % of silicone macromer of formula:

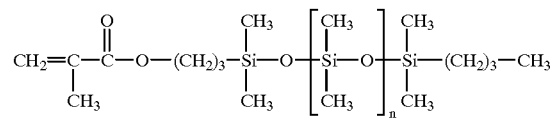

with n being a number chosen so that the number-average molecular weight of the macromer is between approximately 9000 and 12,000, the percentages by weight being calculated with respect to the total weight of the monomers.

Example 2
Aerosol Spray

| | |
|---|---|
| - Grafted silicone polymer of formula (IV) of polymethyl/methyl-siloxane structure with poly(meth-acrylic acid)-3-thiopropyl groups and poly(methyl methacrylate)-3-thiopropyl groups | 3.75 g of AM |
| - Grafted silicone polymer of structure (1) as defined above | 3.75 g of AM |
| - Aminomethylpropanol, 100% neutralization of the two grafted | q.s. for pH 7.5 |

-continued

| silicone polymers | |
|---|---|
| - Ethanol | q.s. for 100 g |

Pressurization scheme:

| - Above composition | 80 g |
|---|---|
| - isobutane | 15 g |
| - 1,1-Difluoroethane | 5 g |

Example 3

Styling Gel

| - Grafted silicone polymer of formula (IV) of polymethyl/methyl-siloxane structure with poly(methacrylic acid)-3-thiopropyl groups and poly(methyl methacrylate)-3-thiopropyl groups | 1 g of AM |
|---|---|
| - Grafted silicone polymer of structure (1) as defined above | 1 g of AM |
| - Crosslinked poly(acrylic acid) sold under the name Synthalen K by the company 3V | 0.5 g of AM |
| - Aminomethylpropanol | q.s. for pH 7.5 |
| - Demineralized water | q.s. for 100 g |

Example 4

Styling Foam

| - Grafted silicone polymer of formula (IV) of polymethyl/methyl-siloxane structure with poly(methacrylic acid)-3-thiopropyl groups and poly(methyl methacrylate)-3-thiopropyl groups | 1 g of AM |
|---|---|
| - Grafted silicone polymer of structure (1) as defined above | 1 g of AM |
| - Acrylic acid/vinylpyrrolidone/lauryl methacrylate (68/23/9%) terpolymer sold under the name Acrylidone LM by the company ISP | 0.5 g of AM |
| - Aminomethylpropanol | q.s. for pH 7.5 |
| - Demineralized water | q.s. for 100 g |

Pressurization scheme:

| - Above composition | 90 g |
|---|---|
| - Isobutane/propane/butane (23/55/22) mixture sold under the name Aerogaz 3.2 N by the Company Elf Aquitaine | 10 g |

Comparative Examples (I) Comparative Examples with Respect to Fixing Power

The fixing power of the three following formulations A, B and C with respect to hair was studied and compared:

Composition A (Prior Art)

| - Grafted silicone polymer $P_1$ of formula (IV) of polymethyl/methylsiloxane structure with poly(methacrylic acid)-3-thio-propyl groups and poly(methyl methacrylate)-3-thiopropyl groups | 5 g of AM |
|---|---|
| - Tripropylene glycol monomethyl ether (plasticizer) | 0.5 g |
| - Aminomethylpropanol, 100% neutralization of the grafted silicone polymer | q.s. for pH 7.5 |
| - 98.5% Ethanol | q.s. for 100 g |

Composition B (Prior Art)

| - Grafted silicone polymer $P_2$ of structure (1) as defined above | 5 g of AM |
|---|---|
| - Tripropylene glycol monomethyl ether (plasticizer) | 0.1 g |
| - Aminomethylpropanol, 100% neutralization of the grafted silicone polymer | q.s. for pH 7.5 |
| - 98.5% Ethanol | q.s. for 100 g |

Composition C (Invention)

| - Grafted silicone polymer $P_1$ of formula (IV) of polymethyl/methylsiloxane structure with poly(methacrylic acid)-3-thio-propyl groups and poly(methyl methacrylate)-3-thiopropyl groups | 2.5 g of AM |
|---|---|
| - Grafted silicone polymer $P_2$ of structure (1) as defined above | 2.5 g of AM |
| - Tripropylene glycol monomethyl ether (plasticizer) | 0.5 g |
| - Aminomethylpropanol 100% neutralization of the grafted silicone polymers | q.s. for pH 7.5 |
| - 98.5% Ethanol | q.s. for 100 g |

Procedure

A measurement test was carried out on the strength of the bonds formed between hairs by a hair lacquer according to the principles of the method described in the article by R. Randall Wickett, John A. Sramek and Cynthia M. Trobaugh in the review *Journ. Soc. Cosmet. Chem.*, 43, 169–178 (May/June 1992).

For each formulation tested, a single hair was taken. A single curl, having a diameter of approximately 2 cm, was produced on the hair by means of a cylindrical support. The hair, thus curled, was steeped in the formulation and was left to dry under a conditioned atmosphere (20° C. and 50% humidity). The curl, fixed by the formulation A, B or C, was cut. 2 half-hairs, bonded to one another via an attachment point, were thus obtained.

The ends, situated on either side of the attachment point, were attached to each of the 2 jaws of a device of the Instron® type, which measures the tensional force in newtons exerted on the half-hairs.

The mean force (over ten tests) $F_A$, $F_B$ and $F_C$ (specific to the compositions A, B and C, respectively) necessary to break the attachment point connecting the two half-hairs formed by the formulation A, B or C was measured.

The improvement with respect to the fixing power introduced by the combination of the grafted silicone polymers $P_1+P_2$ with respect to each of these polymers used alone was determined by calculating the relative variation in the break force, expressed as percentage, measured according to the following formula:

$$[(F_C-F_A)/F_A] \times 100$$

or $$[(F_C-F_B)/F_B] \times 100$$

The results are shown in the table below:

| FORMULATION TESTED | MEAN BREAK FORCE EXPRESSED IN NEWTONS | IMPROVEMENT IN THE BEHAVIOR OF THE FORMULATION C WITH RESPECT TO THE FORMULATION A OR B (AS %) |
|---|---|---|
| C ($P_1 + P_2$) | 0.24 | — |
| A ($P_1$) | 0.09 | +166% |
| B ($P_2$) | 0.19 | +26% |

It was found that the formulation C, containing the combination of polymers $P_1+P_2$, results in a greater fixing power for hair than that obtained with the composition A and the composition B respectively containing the polymer $P_1$ alone and the polymer $P_2$ alone.

(II) Comparative Tests with Respect to the Smoothness to the Touch

A sensory appraisal test was also carried out with respect to a panel of 5 people. The smoothness to the touch after application on the hair of each of the three compositions A, B and C as described above was studied as cosmetic criterion.

The 5 people questioned estimated that the composition C containing the combination of polymers $P_1+P_2$ introduced, to the hair, greater smoothness to the touch than that obtained with the composition A and the composition B, which contained the polymer $P_1$ alone and the polymer $P_2$ alone, respectively.

We claim:

1. A cosmetic or dermatological composition for the treatment of a keratinous substance, comprising, in a cosmetically or dermatologically acceptable medium, (1) at least one grafted silicone polymer having a non-silicone organic skeleton grafted by at least one polysiloxane monomer, and (2) at least one polymer having a polysiloxane skeleton grafted by at least one non-silicone organic monomer.

2. A cosmetic or dermatological composition for the treatment of a keratinous substances, comprising, in a cosmetically or dermatologically acceptable medium, (1) at least one silicone polymer comprising an organic skeleton formed from at least one non-silicone organic monomer and at least one polysiloxane monomer, and (2) at least one polymer having a polysiloxane skeleton grafted by at least one non-silicone organic monomer.

3. A composition according to claim 2, wherein said at least one non-silicone organic monomer is selected from monomers with ethylenic unsaturation polymerizable by the radical route, monomers polymerizable by polycondensation, and monomers with ring opening capacity.

4. A composition according to claim 1, wherein said at least one grafted silicone polymer having a non-silicone organic skeleton is a copolymer comprising:
   a) from 0 to 98 weight % of at least one residue of a lipophilic monomer (A) of low polarity with ethylenic unsaturation of low polarity that is polymerizable by the radical route;
   b) from 0 to 98 weight % of at least one residue of a polar hydrophilic monomer (B) with ethylenic unsaturation that is copolymerizable with said at least one lipophilic monomer (A);
   c) from 0.01 to 50 weight % of at least one residue of a polysiloxane macromer (C) of general formula:

$$X(Y)_n Si(R)_{3-m} - Z_m \quad (I)$$

where:
   X is a vinyl group which is copolymerizable with said monomers (A) and (B);
   Y is a group with divalent bonding;
   R is hydrogen, a $C_1$–$C_6$ alkyl, a $C_1$–$C_6$ alkoxy or a $C_6$–$C_{12}$ aryl;
   Z is a monovalent polysiloxane unit having a number-average molecular weight of at least 500;
   n is 0 or 1; and
   m is an integer ranging from 1 to 3,
   the percentages being calculated with respect to the total weight of said monomers (A) and (B) and said macromer (C), and wherein at least one residue of monomer (A) or monomer (B) is present.

5. A composition according to claim 4, wherein said at least one lipophilic monomer (A) is selected from esters of acrylic or methacrylic acid with $C_1$–$C_{18}$ alcohols; styrene; polystyrene macromers; vinyl acetate; vinyl propionate; α-methylstyrene; tert-butylstyrene; butadiene; cyclohexadiene; ethylene; propylene; vinyltoluene; esters of acrylic or methacrylic acid with 1,1-dihydroperfluoroalkanol derivatives; esters of acrylic or methacrylic acid with ω-hydrofluoroalkanol; esters of acrylic or methacrylic acid with fluoroalkylsulphoamidoalcohol; esters of acrylic or methacrylic acid with fluoroalkyl alcohol; and esters of acrylic or methacrylic acid with alcohol fluoroether.

6. A composition according to claim 4, wherein said at least one lipophilic monomer (A) is selected from n-butyl methacrylate, isobutyl methacrylate, tert-butyl acrylate, tert-butyl methacrylate, 2-ethylhexyl methacrylate, methyl methacrylate, 2-(N-butylperfluorooctanesulphonamido)-ethyl acrylate, and 2-(N-methylperfluorooctanesulphonamido)ethyl acrylate.

7. A composition according to claim 4, wherein said at least one polar hydrophilic monomer (B) is selected from acrylic acid, methacrylic acid, N,N-dimethylacrylamide, dimethylaminoethyl methacrylate, quaternized dimethylaminoethyl methacrylate, (meth)acrylamide, N-t-butylacrylamide, maleic acid, maleic anhydride and its half-esters, hydroxyalkyl (meth)acrylates, diallyldimethylammonium chloride, vinylpyrrolidone, vinyl ethers, maleimides, vinylpyridine, vinylimidazole, polar heterocyclic vinyl compounds, styrenesulphonate, allyl alcohol, vinyl alcohol, and vinylcaprolactam.

8. A composition according to claim 7, wherein said at least one polar hydrophilic monomer (B) is selected from acrylic acid, N,N-dimethylacrylamide, dimethylaminoethyl methacrylate, quaternized dimethylaminoethyl methacrylate, and vinylpyrrolidone.

9. A composition according to claim 4, wherein said at least one polysiloxane macromer (C) corresponds to the following general formula (II):

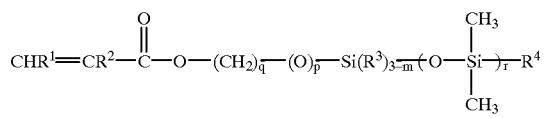

in which:
$R^1$ is hydrogen or —COOH;
$R^2$ is hydrogen, methyl or —$CH_2COOH$;
$R^3$ is $C_1$–$C_6$ alkyl, $C_1$–$C_6$ alkoxy, $C_1$–$C_6$ alkylamino, $C_6$–$C_{12}$ aryl or hydroxyl;
$R^4$ is $C_1$–$C_6$ alkyl, $C_1$–$C_6$ alkoxy, $C_1$–$C_6$ alkylamino, $C_6$–$C_{12}$ aryl or hydroxyl;
q is an integer from 2 to 6;
p is 0 or 1;
r is an integer from 5 to 700; and
m is an integer ranging from 1 to 3.

10. A composition according to claim 4, wherein said at least one polysiloxane macromer (C) corresponds to the following general formula:

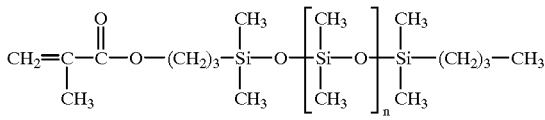

wherein n is a number ranging from 5 to 700.

11. A composition according to claim 1, wherein said at least one polymer having a non-silicone organic skeleton is a copolymer obtained by radical polymerization from the mixture of monomers:
   a) 60 weight % of tert-butyl acrylate;
   b) 20 weight % of acrylic acid; and
   c) 20 weight % of silicone macromer of formula:

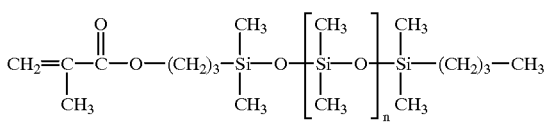

wherein n is a number ranging from 5 to 700, the percentages by weight being calculated with respect to the total weight of the monomers.

12. A composition according to claim 1, wherein said at least one polymer having a non-silicone organic skeleton is a copolymer obtained by radical polymerization from the mixture of monomers:
   a) 80 weight % of tert-butyl acrylate; and
   b) 20 weight % of silicone macromer of formula:

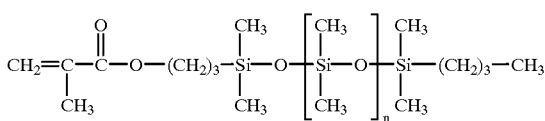

wherein n is a number ranging from 5 to 700, the percentages by weight being calculated with respect to the total weight of the monomers.

13. A composition according to claim 1, wherein said polymer having a non-silicone organic skeleton has a number-average molecular weight ranging from 10,000 to 2,000,000 and has a glass transition temperature Tg or a crystalline melting temperature Tm of at least −20° C.

14. A composition according to claim 1, wherein said at least one grafted silicone polymer is a copolymer obtained by reactive extrusion of a polysilixone monomer, said polysiloxane monomer being a polysiloxane macromer having an end reactive functional group, with a non-silicone organic skeleton, said non-silicone organic skeleton being a polyolefin containing reactive groups capable of reacting with the end reactive functional group of the polysiloxane macromer to form a covalent bond enabling said polysiloxane macromer to be grafted to the polyolefin.

15. A composition according to claim 14, wherein said polyolefin is selected from polyethylenes and polymers of monomers derived from ethylene having reactive functional groups capable of reacting with the end functional group of said polysiloxane macromer.

16. A composition according to claim 14, wherein said polyolefin is selected from copolymers of
   ethylene or of ethylene derivatives and
   at least one monomer selected from monomers containing a carboxyl functional group, monomers containing an acid anhydride functional group, monomers containing an acid chloride functional group, monomers containing an ester functional group, and monomers containing an isocyanate functional group.

17. A composition according to claim 14, wherein said polysiloxane macromer contains a functionalized group at or close to the end of said polysiloxane macromer, wherein said functionalized group is selected from alcohols, thiols, epoxy groups and primary and secondary amines.

18. A composition according to claim 14, wherein said polysiloxane macromer corresponds to the formula (III):

$$T-(CH_2)_s-Si-[-(OSiR^5R^6)_t-R^7]_y \qquad (III)$$

wherein T is selected from $NH_2$, NHR', an epoxy functional group, OH and SH; and wherein $R^5$, $R^6$, $R^7$ and R' independently denote $C_1$–$C_6$ alkyl, phenyl, benzyl, $C_6$–$C_{12}$ alkylphenyl or hydrogen; s is a number from 2 to 100; t is a number from 0 to 1000; and y is a number from 1 to 3.

19. A cosmetic or dermatological composition for the treatment of a keratinous substance, comprising, in a cosmetically or dermatologically acceptable medium, (1) at least one grafted silicone polymer having a non-silicone organic skeleton grafted by at least one polysiloxane monomer, and (2) at least one polymer having a polysiloxane skeleton comprising a main polysiloxane chain formed from at least one polysiloxane monomer and at least one organic group not containing silicone.

20. A composition according to claim 1, wherein said polymer having a polysiloxane skeleton is obtained by radical copolymerization between (a) at least one non-silicone monomer selected from at least one anionic non-silicone organic monomer exhibiting at least one ethylenic unsaturation and at least one hydrophobic non-silicone organic monomer exhibiting at least one ethylenic unsaturation and (b) a polysiloxane exhibiting, in its chain, at least one functional group capable of reacting with said at least one ethylenic unsaturation of said at least one non-silicone monomer.

21. A composition according to claim 20, wherein said at least one anionic non-silicone organic monomer is selected from linear and branched unsaturated carboxylic acids.

22. A composition according to claim 21, wherein said at least one anionic non-silicone organic monomer is selected from acrylic acid, methacrylic acid, maleic acid, maleic anhydride, itaconic acid, fumaric acid, crotonic acid, and alkali metal, alkaline-earth metal, and ammonium salts thereof.

23. A composition according to claim 20, wherein said at least one hydrophobic non-silicone organic monomer is selected from alkanol acrylic acid esters, and alkanol methacrylic acid esters.

24. A composition according to claim 23, wherein, in said alkanol acrylic acid esters, said alkanol is $C_1$–$C_{18}$ alkanol.

25. A composition according to claim 23 wherein, in said alkanol methacrylic acid esters, said alkanol is $C_1$–$C_{18}$ alkanol.

26. A composition according to claim 23, wherein said at least one hydrophobic non-silicone organic monomer is selected from isooctyl (meth)acrylate, isononyl (meth)acrylate, 2-ethylhexyl( meth)acrylate, lauryl (meth)acrylate, isopentyl (meth)acrylate, n-butyl (meth)acrylate, isobutyl (meth)acrylate, methyl (meth)acrylate, tert-butyl (meth) acrylate, tridecyl (meth)acrylate and stearyl (meth)acrylate.

27. A composition according to claim 19, wherein said at least one organic group not containing silicone is an anionic organic group obtained by the radical (homo)polymerization of at least one anionic monomer of unsaturated carboxylic acid type, partially or completely neutralized in the form of a salt.

28. A composition according to claim 1, wherein said at least one polymer having a polysiloxane skeleton is selected from the silicone polymers containing, in their structure, the following unit of formula (IV):

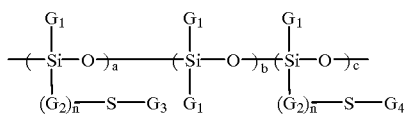

wherein each $G_1$ independently is hydrogen, a $C_1$–$C_{10}$ alkyl radical or a phenyl radical; each $G_2$ independently is a $C_1$–$C_{10}$ alkylene group; $G_3$ is a polymer residue resulting from the (homo)polymerization of at least one anionic monomer with at least one ethylenic unsaturation; $G_4$ is a polymer residue resulting from the (homo)polymerization of at least one hydrophobic monomer with at least one ethylenic unsaturation; m and n each independently is equal to 0 or 1; a is an integer ranging from 0 to 50; b is an integer ranging from 10 to 350 and c is an integer ranging from 0 to 50; with the proviso that one of the parameters a and c is other than 0.

29. A composition according to claim 28, wherein said unit of formula (IV) exhibits at least one of the following characteristics:
  each $G_1$ independently is a $C_1$–$C_{10}$ alkyl radical;
  n is not zero and each $G_2$ independently is a $C_1$–$C_3$ alkylene group;
  $G_3$ is a polymer residue resulting from the (homo) polymerization of at least one carboxylic acid monomer with at least one ethylenic unsaturation; or
  $G_4$ is a polymer residue resulting from the (homo) polymerization of at least one ($C_1$–$C_{10}$)alkyl (meth) acrylate monomer.

30. A composition according to claim 28, wherein in said unit of formula (IV):
  each $G_1$ is a methyl radical;
  n is not zero and each $G_2$ is a propylene group;
  $G_3$ is a polymer residue resulting from the (homo) polymerization of at least one monomer selected from acrylic acid monomers and methacrylic acid monomers; and
  $G_4$ is a polymer residue resulting from the (homo) polymerization of at least one monomer selected from isobutyl monomers and methyl (meth)acrylate monomers.

31. A composition according to claim 1, wherein the number-average molecular mass of said at least one polymer having a polysiloxane skeleton ranges from approximately 10,000 to 1,000,000.

32. A composition according to claim 31, wherein said number-average molecular mass ranges from approximately 10,000 to 100,000.

33. A composition according to claim 1, wherein said at least one grafted silicone polymer having a non-silicone organic skeleton is present in said cosmetic or dermatological composition in an amount ranging from 0.01 to 20 weight % with respect to the total weight of said composition.

34. A composition according to claim 33, wherein said at least one grafted silicone polymer having a non-silicone organic skeleton is present in said cosmetic or dermatological composition in an amount ranging from 0.1 to 15 weight %.

35. A composition according to claim 33, wherein said at least one grafted silicone polymer having a non-silicone organic skeleton is present in said cosmetic or dermatological composition in an amount ranging from 0.5 to 10 weight %.

36. A composition according to claim 1, wherein said at least one polymer having a polysiloxane skeleton is present in said cosmetic or dermatological composition in an amount ranging from 0.01 to 20 weight % with respect to the total weight of the composition.

37. A composition according to claim 36, wherein said at least one polymer having a polysiloxane skeleton is present in said cosmetic or dermatological composition in an amount ranging from 0.1 to 15 weight %.

38. A composition according to claim 36, wherein said at least one polymer having a polysiloxane skeleton is present in said cosmetic or dermatological composition in an amount ranging from 0.5 to 10 weight %.

39. A composition according to claim 1, further comprising at least one additive, wherein said additive is a thickener, fatty acid ester, ester of fatty acids and of glycerol, silicone, surfactant, fragrance, preservative, sunscreening agent, protein, vitamin, polymer, a vegetable, animal, mineral or synthetic oil or mixtures thereof.

40. A composition according to claim 1, wherein said cosmetically or dermatologically acceptable medium comprises water or a mixture of water and at least one cosmetically acceptable solvent.

41. A composition according to claim 33, wherein said at least one cosmetically acceptable solvent is selected from monoalcohols, polyalcohols, glycol ethers, and fatty acid esters.

42. A composition according to claim 1, wherein said at least one polymer having a polysiloxane skeleton is dissolved in said cosmetically or dermatologically acceptable medium or is present in said composition in the form of an aqueous dispersion of particles.

43. A composition according to claim 1, wherein said keratinous substance is human hair.

44. A composition according to claim 1, wherein said composition is in the gel, milk, cream, lotion or foam form.

45. A composition according to claim 1, wherein said composition is a styling product.

46. A composition according to claim 1, wherein said composition is a hair product which is or is not to be rinsed out.

47. A composition according to claim 46, wherein said hair product is a shampoo.

48. A composition according to claim 1, wherein said composition is a hair product which is to be applied before or after shampooing, dyeing, bleaching, permanent waving or hair straightening.

49. A composition according to claim 1, wherein said composition is packaged in the form of a vaporizer or pump-action spray, or in an aerosol container for the purpose of obtaining a spray, a lacquer or a foam.

50. A process for the treatment of at least one keratinous substance, comprising the step of applying to said at least one keratinous substance a composition according to claim 1.

51. A process according to claim 50, further comprising the step of rinsing at least one keratinous substance with water.

52. A process according to claim 50, wherein said at least one keratinous substance is hair.

53. A composition according to claim 1, wherein said at least one grafted silicone polymer is a copolymer comprising:
  a) 60 weight % of residues of tert-butyl acrylate;

b) 20 weight % of residues of acrylic acid; and
c) 20 weight % of residues of silicone macromer of formula:

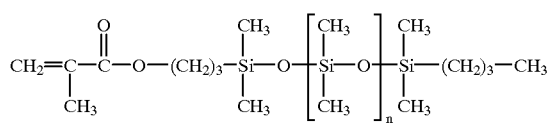

wherein n is a number ranging from 5 to 700, the percentages by weight being calculated with respect to the total weight of the residues of the monomers.

54. A composition according to claim 1, wherein said at least one grafted silicone polymer is a copolymer comprising:
a) 80 weight % of residues of tert-butyl acrylate; and
b) 20 weight % of residues of silicone macromer of formula:

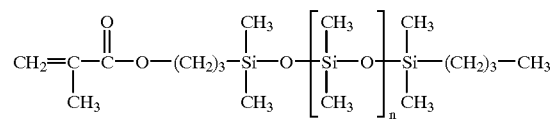

wherein n is a number ranging from 5 to 700, the percentages by weight being calculated with respect to the total weight of the residues of the monomers.

* * * * *